United States Patent [19]

Hsieh

[11] Patent Number: 5,594,767
[45] Date of Patent: Jan. 14, 1997

[54] METHODS AND APPARATUS FOR ENHANCING IMAGE SHARPNESS

[75] Inventor: Jiang Hsieh, Waukesha, Wis.

[73] Assignee: General Electric Company, Milwaukee, Wis.

[21] Appl. No.: 556,745

[22] Filed: Nov. 2, 1995

[51] Int. Cl.$^6$ ............................................. A61B 6/03
[52] U.S. Cl. ............................ 378/8; 378/901; 364/413.17
[58] Field of Search ......................... 364/413.17, 413.19, 364/413.23; 378/4, 8, 901

[56] References Cited

U.S. PATENT DOCUMENTS

| | | | |
|---|---|---|---|
| 4,739,481 | 4/1988 | Yoshitome | 364/413.19 |
| 4,813,528 | 5/1989 | Crawford et al. | 364/413.22 |
| 4,821,213 | 4/1989 | Cline et al. | 364/522 |
| 4,831,528 | 4/1990 | Crawford | 364/413.17 |
| 4,839,805 | 6/1989 | Pearson, Jr. et al. | 364/413.14 |
| 4,879,668 | 11/1989 | Cline et al. | 364/522 |
| 5,166,876 | 11/1992 | King et al. | 364/413.13 |
| 5,233,518 | 8/1993 | King et al. | 364/413.18 |
| 5,265,142 | 11/1993 | Hsieh | 378/4 |
| 5,270,923 | 12/1993 | King et al. | 364/413.13 |
| 5,400,377 | 3/1995 | Hu et al. | 387/8 |
| 5,416,815 | 5/1995 | Hsieh | 378/4 |
| 5,473,655 | 12/1995 | Hu | 378/4 |

OTHER PUBLICATIONS

H. E. Johns & J. R. Cunningham. The Physics of Radiology, Charles C. Thomas, 1983, p. 164, no month.
L. L. Berland, Practical CT, Technology and Techniques, Raven Press, New York, 1986, p. 94, no month.

*Primary Examiner*—Michael J. Tokar
*Assistant Examiner*—David Vernon Bruce
*Attorney, Agent, or Firm*—John S. Beulick; John H. Pilarski

[57] ABSTRACT

The present invention, in one form, is a method for enhancing image sharpness in images generated from CT scan data by using enhancement masks. The enhancement masks are generated, in one embodiment, by generating difference image data from the original age data and low pass filtered image data. The original image data CT numbers are assigned to image regions, e.g., bone, air, and soft tissue, and based on such CT number classifications, certain data in the difference image is fully or partially suppressed. Subsequent to suppressing some difference image data, the difference image data set, which is sometimes referred to as an enhancement mask, is then combined With the original image data to increase image sharpness.

20 Claims, 2 Drawing Sheets

METHODS AND APPARATUS FOR ENHANCING IMAGE SHARPNESS

FIELD OF THE INVENTION

This invention relates generally to computed tomography (CT) imaging and more particularly, to improving the quality of an image by using enhancement masks and edge enhancement techniques.

BACKGROUND OF THE INVENTION

In at least one known CT system configuration, an x-ray source projects a fan-shaped beam which is collimated to lie within an X-Y plane of a Cartesian coordinate system, generally referred to as the "imaging plane". The x-ray beam passes through the object being imaged, such as a patient. The beam after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view" A "scan" of the object comprises a set of views made at different gantry angles during one revolution of the x-ray source and detector. In an axial scan, the projection data is processed to construct an image that corresponds to a two dimensional slice taken through the object.

One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a cathode ray tube display.

To reduce the total scan time required for multiple slices, a "helical" scan may be performed. To perform a "helical" scan, the patient is moved in the z-axis synchronously with the rotation of the gantry, while the data for the prescribed number of slices is acquired. Such a system generates a single helix from a fan beam helical scan. The helix mapped out by the fan beam yields projection data from which images in each prescribed slice may be reconstructed. In addition to reduced scanning time, helical scanning provides other advantages such as better control of contrast, improved image reconstruction at arbitrary locations, and better three-dimensional images.

Efforts have been undertaken to enhance the quality of inner auditory canal (IAC) structure images. The most significant image quality issues with IAC structures include a lack of "sharpness" in the IAC structure and excessive aliasing artifacts that obstruct human anatomy. With a third generation scanner, if the detector and x-ray focal spot response are modeled as square waveforms, it can be shown that two samples within each detector cell width are required to eliminate aliasing artifacts.

In some known third generation scanners, it is not possible to obtain such samples. Other known scanners employ x-ray focal spot wobbling in an attempt to obtain sufficient samples. Tube design complexity, tube reliability, detector temporal response, and resources impact concerns all arise when focal spot wobbling is employed.

Still other known scanners employ quarter detector offset in an attempt to reduce aliasing artifacts. Particularly, by aligning the iso-center of the system and the center of the detector a quarter of a detector cell apart, interleaved samples can be obtained near the detector center when $2\pi$ views of projection data are acquired. However, quarter detector offset is limited in that the data interleaving is only near perfect at the detector center, and at locations spaced from the detector center, the sampling pattern is not perfectly interleaved. Therefore, quarter detector offset generally only is effective at eliminating aliasing artifacts near the iso-center.

In addition to eliminating, or reducing, aliasing artifacts, it generally is desirable to enhance the "sharpness" of an image. Image enhancement techniques, such as highlighting the edges of an image, are known. However, such techniques, while enhancing "sharpness", also tend to increase image noise and aliasing artifacts. As a result, known image sharpness enhancement techniques sometimes reduce the overall image quality.

Particularly with IAC images, a high level image sharpness and a low level of aliasing artifacts are desired. It also is desirable to increase image sharpness and decrease the level of aliasing artifacts without reducing overall image quality.

SUMMARY OF THE INVENTION

These and other objects may be obtained in a system which, in one embodiment, utilizes enhancement masks to reduce image noise and aliasing artifacts while enhancing image "sharpness" for an IAC structure. Particularly, in accordance with one embodiment of the present invention, once CT numbers are generated for an image, a classification map is generated for the CT numbers by assigning each CT number to certain regions or classes, such as "bone", "air" and "soft tissue" regions. A difference image also is generated by low pass filtering the original image data and subtracting the low pass filtered image data from the original image data. The original image data, of course, also is preserved.

An enhancement mask is then generated using the CT classification map and the difference image data. Particularly, based on the CT number classifications, some data in the difference image is suppressed. For example, in the soft tissue regions, the CT numbers in the difference image are set about to zero. In all other regions, e.g., bone and air regions, the CT numbers in the difference image are preserved.

A combined image data set is generated which has smoothed image data for the soft tissue regions and original image data for the bone-air regions. The enhancement mask is then added to the combined image data set. As a result, the enhancement mask is added to the original image data for bone and air regions, and the enhancement mask is added to the smoothed image data for the soft tissue regions.

Using the above described image enhancement algorithm, image noise and aliasing artifacts are reduced while image sharpness is enhanced. Further, the overall image quality is not reduced.

DETAILED DESCRIPTION OF THE DRAWINGS

Figure 1:
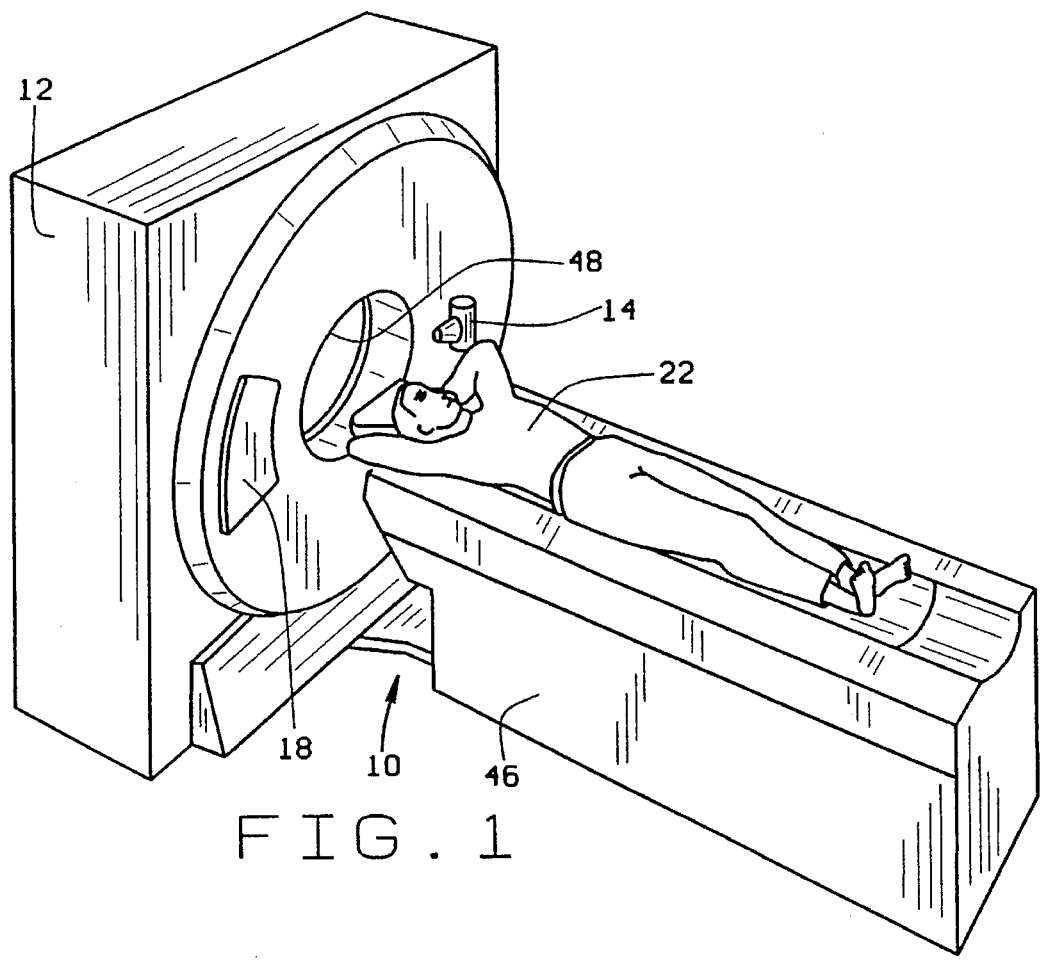
FIG. 1 is a pictorial view of a CT imaging system.
Figure 2:
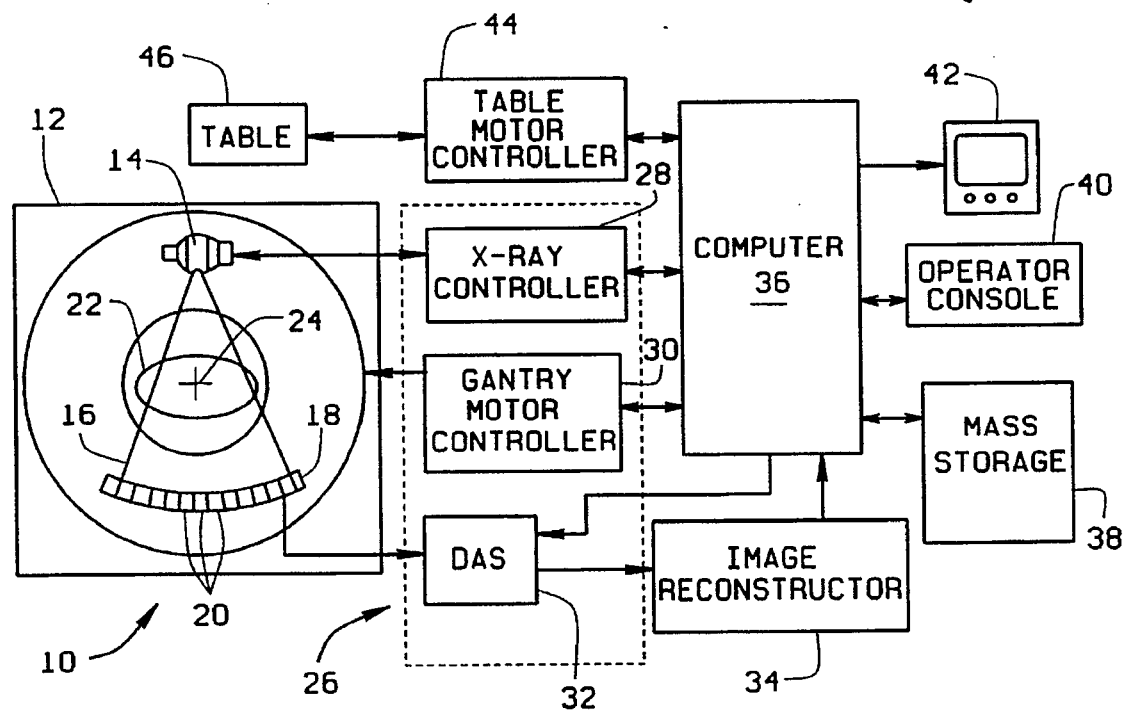
FIG. 2 is a block schematic diagram of the system illustrated in FIG. 1.

Referring to FIGS. 1 and 2, a computed tomograph (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements 10 which together sense the projected x-rays that pass through a medical patient 22. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38. Preferably, the reconstructed image is stored as a data array.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

The following discussion of image enhancement sometimes refers specifically to enhancing images of IAC structures. The image enhancement algorithm, however, is not limited to practice in connection with only IAC structures and may be used to enhance images of other structures. It should be further understood that the image enhancement algorithm would be implemented in computer 36 and would process, for example, image data stored in mass storage 38. Alternatively, the image enhancement algorithm could be implemented in image reconstructor 34 and supply image enhanced data to computer 36. Other alternative implementations are, of course, possible.

Figure 3:
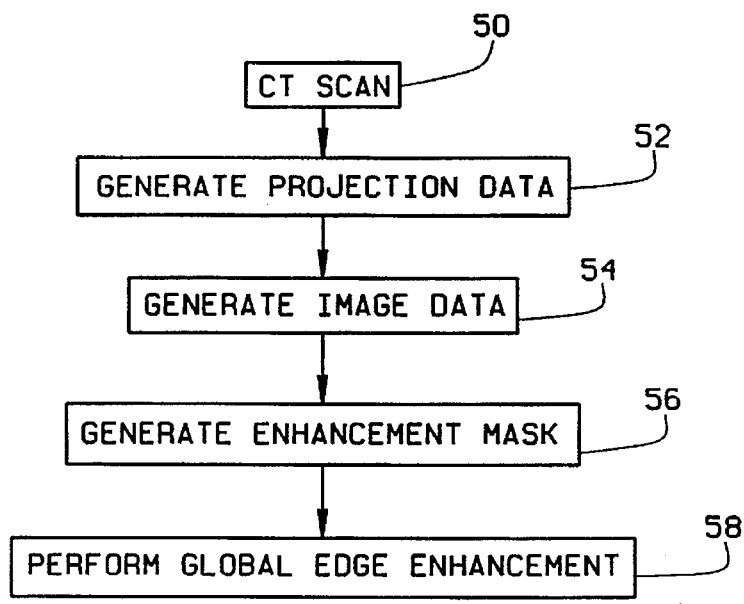
FIG. 3 illustrates a sequence of steps executed in accordance with one embodiment of the image enhancement method.

Referring to FIG. 3, and as described above, in performing a CT scan 50, data from detector elements 20 is obtained. Such data is generally referred to in the art as projection data 52. High speed image reconstruction is then performed to generate image data 54. With respect to image reconstruction, many image reconstruction algorithms currently are implemented in commercially available CT machines and the present image enhancement algorithm could be implemented in connection with many of such reconstruction algorithms.

In practicing the present image enhancement algorithm, it is desirable to utilize original image data representing a sharp image with a low level of artifacts. One image reconstruction algorithm which generates such image data is generally referred to as the Bone algorithm and currently is implemented in third generation CT systems commercially available from General Electric Company, Milwaukee, Wisconsin. In such systems, the projection data is pre-processed, filtered, and then backprojected. In the filtering step, the cutoff frequency of the filter kernel can be modified to make the final reconstructed image either smoother or sharper. In addition, the Nyquist sampling frequency for a single fan beam is $N_y$, and the cutoff frequency of the Bone algorithm filter is $1.8\,N_y$. The shape of the filter kernel may be modified to boost mid-frequency content to further sharpen the image. The present invention, as explained above, is not directed to image reconstruction algorithms such as the Bone algorithm. Rather, the present image enhancement systems and algorithms may be used in connection with such image reconstruction algorithms.

Referring again to FIG. 3, and after generation of the original image data 54, an enhancement mask 56 is generated. Generation of such enhancement mask is described below in more detail. The enhancement mask is utilized in performing global edge enhancement 58, which also is described below in more detail.

Figure 4:
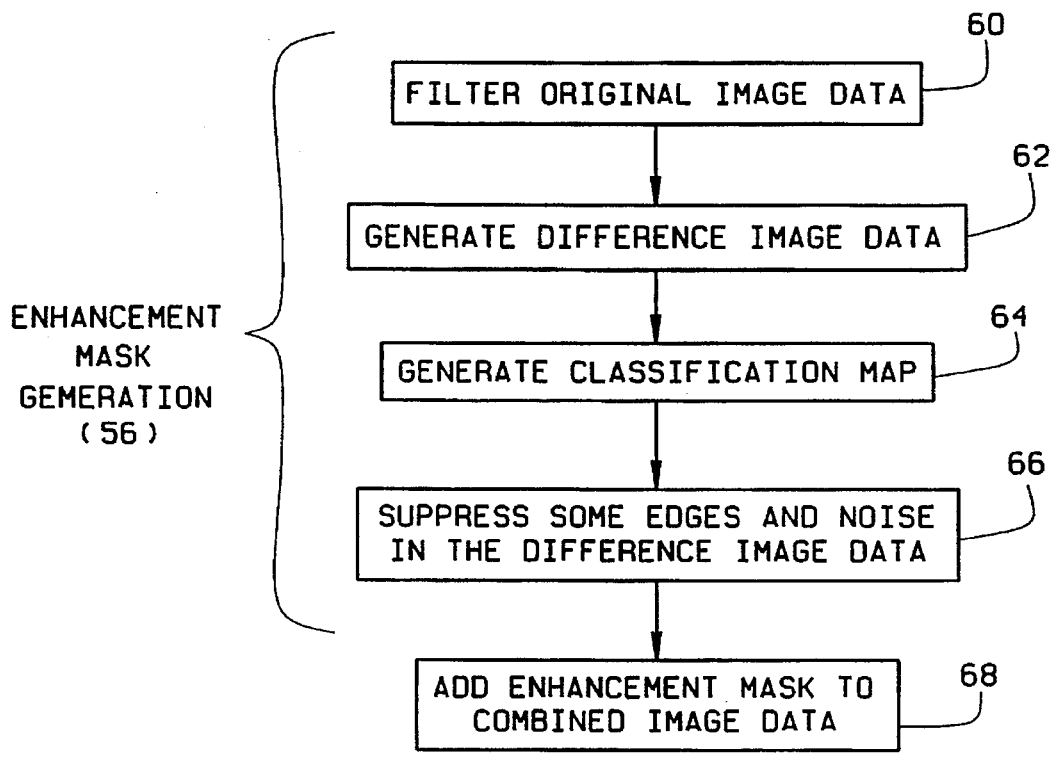
FIG. 4 illustrates a sequence of steps executed in accordance with the global edge enhancement step illustrated in FIG. 3.

With reference to FIG. 4, to generate the enhancement mask, the original image data is low pass filtered 60 to generate smoothed image data. The low pass filter may, for example, be a boxcar smoothing filter, where each pixel reading, or CT number, is replaced by the average of its N nearest neighbors, including itself. However, many other filters may be used, such as a Gaussian shaped filter. Such low pass filtering is well known in the art. The smoothed image data is then subtracted from the original image data to obtain "edge only", or difference, image data 62. The difference image data contains all image edge and image noise information.

Alternatively, rather than the low pass filter and subtraction operations described above, other algorithms may be used to obtain the difference image data. For example, a high pass filter may be used to obtain the difference image data directly. High pass filter algorithms are well known in the art.

In addition to generating the difference image dam, a classification map also is generated 64. CT numbers from the original image data may be used in generating the classification map. Particularly, each CT number in the original image data is assigned to a certain class, or region, based on its intensity. In general, different materials have different CT numbers. For example, bone has a CT number of over 200, water has a CT number of 0, grey-white matter (or soft tissue) in the brain has a CT number from approximately 20–50, and air has a CT number of −1000. Since the CT numbers are different for various regions, a thresholding method can generally be used to assign CT numbers to certain classes, e.g., bone, water, soft tissue, and air.

Many CT numbers, however, have intensities which fall between classes, or thresholds. To assign such CT numbers to appropriate classes, fuzzy logic can be used. For example, for a CT number of 80, the CT number could not be assigned, with great confidence, either to bone or to grey-white matter. Conversely, this CT number has a dual membership to both the bone class and the grey-white matter class. Utilizing fuzzy logic, the CT number may be determined to belong to grey-white matter class with a membership grade of 0.6, for example, and belong to bone class with a membership grade of 0.4. The transition function from the grey-white matter region to the bone region can be either linear or non-linear functions. For example, an S-function, which is well known in the Fuzzy logic art, can be utilized. As a result of the above described process, each pixel, or CT number, in the image data is assigned to a certain class.

Prior to classifying the pixels or CT numbers, the original image data can be smoothed to reduce the impact of noise on the pixel classification. For example, the original image data can be low pass filtered to reduce the influence of statistical noise on the image classification.

After classifying the pixels as described above, a classification map of the image is generated. Specifically, and with respect to the classification map, the bone and air regions, where enhancement generally is desired, are assigned a value of one. The soft tissue regions are assigned a value of zero. The dual membership regions are assigned a value between zero and one based on their membership grade.

After generation of the classification map, some difference image data is suppressed 66. Such suppression is performed by multiplying the classification map and the difference image data. As a result of such multiplication, CT numbers in regions that are classified "soft tissue" are set to near zero in the difference image data. In the "fuzzy" regions, the edge information is partially suppressed, or scaled, based on the "grade" of the membership function. Specifically, based on the membership grade, a new value is generated to control the amount of edge enhancement. For example, assuming the difference image data at a fuzzy pixel location has a value of $\epsilon$, and the membership grade for this pixel is 0.6 grey-white matter and 0.4 bone, the resulting edge data for this location is then $0.4\epsilon$. These suppressions can be implemented by other, not necessarily linear, functions. The amount of scaling depends on the amount of edge enhancement desired. In regions other than soft tissue regions and fuzzy regions, the edge information in the difference image data is fully preserved. The difference image data set, subsequent to the suppression operation, is sometimes referred to herein as the enhancement mask.

The enhancement mask image data may, of course, be linearly or non-linearly scaled depending upon the amount of image enhancement desired. In other words, the enhancement mask image data represents a candidate of the amount of enhancement to be added to the original, or smoothed, image data. The amount of the enhancement to be added to the image data may be modified, as desired.

A combined image data set also is generated. The combined image data set includes both original image data and smoothed image data. More specifically, since bone and air regions are to be enhanced, the original image data is multiplied by the classification map to maintain only the original image data for bone-air regions in a first set of image data. For soft tissue regions that are not to be enhanced, the smoothed image data is multiplied by the inverse of the classification map so that the regions corresponding to bone and air are zeros, and the soft tissue region smoothed image data is maintained in a second set of image data. The first and second image data sets are then added together to generate the combined image data set having the original image data for the bone-air regions and the smoothed image data for the soft tissue region.

The enhancement mask image data is then added to the combined image data set 68. As a result, the enhancement mask image data for soft tissue regions and fuzzy regions is combined, or added to, the smoothed original image data to further suppress noise and aliasing artifacts. For regions classified as "bone" or "air", the enhancement mask image data is added to the original image data to enhance the original image data for such regions.

The above described algorithm, which includes generation of the enhancement mask, increases image sharpness and reduces the levels of image noise and aliasing artifacts. Such desired results are provided without adversely affecting overall image quality.

From the preceding description of the present invention, it is evident that the objects of the invention are attained. Although the invention has been described and illustrated in detail, it is to be clearly understood that the same is intended by way of illustration and example only and is not to be taken by way of limitation. For example, the present invention can be used to enhance image data for regions other than IAC. Also, while the CT system described herein is a "third generation" system, many other CT systems, such as "fourth generation" systems may be used. Accordingly, the spirit and scope of the invention are to be limited only by the terms of the appended claims.

What is claimed is:

1. A method for enhancing original image data represented as CT numbers, said method comprising the steps of:

generating, from the CT numbers, an enhancement mask said step of generating an enhancement mask comprising the steps of:

generating a classification map by designating a plurality of CT number classes based on CT number values and assigning the CT numbers to certain classes to generate the classification map; and generating a difference image by filtering the original image data to generate low pass filtered image data and subtracting the low pass filtered data from the original image data; and generating an edge enhanced image utilizing the enhancement mask and the CT numbers.

2. A method in accordance with claim 1 wherein generating an edge enhanced image comprises the step of:

adding the enhancement mask data to at least some of the original image data.

3. A method in accordance with claim 1 wherein generating an edge enhanced image comprises the steps of:

smoothing the original image data to generate smoothed image data;

adding the enhancement mask data to the smoothed image data corresponding to regions which are not to be enhanced; and adding the enhancement mask data to the original image data corresponding to the regions which are to be enhanced.

4. A method in accordance with claim 3 wherein smoothing the original image data comprises the step of:

filtering the original image data to generate low pass filtered data.

5. A method in accordance with claim 1 wherein generating the enhancement mask further comprises the step of:

scaling the difference image data using the CT number assignments.

6. A method in accordance with claim 5 wherein scaling the difference image data comprises the step of:

applying a linear function to the difference image data using the CT number assignments.

7. A method in accordance with claim 1 wherein assigning the CT numbers to certain classes comprises the steps of:

establishing threshold values for different image regions;

if a particular CT number satisfies a particular threshold criteria for an image region, classifying the particular CT number as a member of the image region; and if a particular CT number satisfies no threshold criteria for an image region, utilizing a fuzzy logic function to determine a membership grade for the CT number.

8. A method in accordance with claim 7 wherein the fuzzy logic function comprises an S-function.

9. A method in accordance with claim 7 wherein generating an enhancement mask further comprises the steps of:

filtering the original image data to generate low pass filtered image data;

generating difference image data by subtracting the low pass filtered data from the original image data; and generating the enhancement mask using the difference image data and the CT number classifications.

10. A method in accordance with claim 9 wherein generating an edge enhanced image comprises the step of:

adding the enhancement mask data to at least some of the original image data.

11. A method in accordance with claim 9 wherein generating an edge enhanced image comprises the steps of:

smoothing the original image data to generate smoothed image data;

adding the enhancement mask data to the smoothed image data corresponding to regions which are not to be enhanced; and adding the enhancement mask data to the original image data corresponding to the regions which are to be enhanced.

12. A system for enhancing original image data represented as CT numbers, said system configured to:

generate an enhancement mask using the CT numbers, and wherein to generate the enhancement mask, said system is configured to:

generate a classification map by assigning CT numbers a certain classification based on the CT number value, generate a difference image by filtering the original image data to generate low pass filtered image data and subtracting the low pass filtered data from the original image data; and generate an edge enhanced image utilizing the enhancement mask and the CT numbers.

13. A system in accordance with claim 12 wherein to generate an edge enhanced image, said system is configured to:

add the enhancement mask data to at least some of the original image data.

14. A system in accordance with claim 12 wherein to generate an edge enhanced image, said system is configured to:

smooth the original image data to generate smoothed image data;

add the enhancement mask data to the smoothed image data corresponding to regions which are not to be enhanced; and add the enhancement mask data to the original image data corresponding to the regions which are to be enhanced.

15. A system in accordance with claim 12 wherein to generate an enhancement mask, said system is further configured to:

scale the difference image data using the CT number classifications.

16. A system in accordance with claim 12 wherein to assign CT numbers to certain classes, said system is configured to:

establish threshold values for different image regions;

if a particular CT number satisfies a particular threshold criteria for an image region, classify the particular CT number as being a member of the image region; and if a particular CT number satisfies no threshold criteria for an image region, utilize a fuzzy logic function to determine a membership grade for the CT numbers.

17. A method for enhancing original image data represented as CT numbers, said method comprising the steps of:

generating, from the CT numbers, an enhancement mask, said step of generating an enhancement mask comprising the steps of:

designating a plurality of CT number classes based on CT number values; and assigning the CT numbers to certain classes to generate a classification map, said step of assigning the CT numbers to certain classes comprising the steps of:

establishing threshold values for different image regions;

if a particular CT number satisfies a particular threshold criteria for an image region, classifying the particular CT number as a member of the image region; and if a particular CT number satisfies no threshold criteria for an image region, utilizing a fuzzy logic function to determine a membership grade for the CT number; and generating an edge enhanced image utilizing the enhancement mask and the CT numbers.

18. A method in accordance with claim 12 wherein generating an enhancement mask further comprises the steps of:

filtering the original image data to generate low pass filtered image data;

generating difference image data by subtracting the low pass filtered data from the original image data; and generating the enhancement mask using the difference image data and the CT number classifications.

19. A method in accordance with claim 17 wherein generating an edge enhanced image comprises the step of:

adding the enhancement mask data to at least some of the original image data.

20. A method in accordance with claim 17 wherein generating an edge enhanced image comprises the steps of:

smoothing the original image data to generate smoothed image data;

adding the enhancement mask data to the smoothed image data corresponding to regions which are not to be enhanced; and adding the enhancement mask data to the original image data corresponding to the regions which are to be enhanced.

* * * * *